(12) United States Patent
Parthasaradhi Reddy et al.

(10) Patent No.: US 8,106,210 B2
(45) Date of Patent: Jan. 31, 2012

(54) POLYMORPHS OF ESOMEPRAZOLE SALTS

(75) Inventors: Bandi Parthasaradhi Reddy, Andhrapradesh (IN); Kura Rathnakar Reddy, Hyderabad (IN); Rapolu Raji Reddy, Hyderabad (IN); Dasari Muralidhara Reddy, Hyderabad (IN); Puchakayala Srinivasa Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 14 days.

(21) Appl. No.: 12/374,347

(22) PCT Filed: Oct. 8, 2007

(86) PCT No.: PCT/IN2007/000466
§ 371 (c)(1),
(2), (4) Date: Jan. 19, 2009

(87) PCT Pub. No.: WO2009/047775
PCT Pub. Date: Apr. 16, 2009

(65) Prior Publication Data
US 2010/0227890 A1 Sep. 9, 2010

(51) Int. Cl.
*C07D 401/12* (2006.01)
(52) U.S. Cl. .................................................. 546/273.7
(58) Field of Classification Search ................ 546/273.7
See application file for complete search history.

(56) References Cited

U.S. PATENT DOCUMENTS

| | | | |
|---|---|---|---|
| 4,738,974 A | 4/1988 | Briindstrom | |
| 5,714,504 A | 2/1998 | Lindberg et al. | |
| 5,877,192 A | 3/1999 | Lindberg et al. | |
| 6,369,085 B1 | 4/2002 | Cotton et al. | |
| 2008/0076929 A1 | 3/2008 | Parthasaradhi Reddy | |

FOREIGN PATENT DOCUMENTS

| | | |
|---|---|---|
| EP | 0005129 B1 | 4/1981 |
| WO | 9427988 A1 | 12/1994 |
| WO | 9602535 A1 | 2/1996 |
| WO | 9828294 A1 | 7/1998 |
| WO | 9854171 A1 | 12/1998 |
| WO | 2004002982 A2 | 1/2004 |
| WO | 2004020436 A1 | 3/2004 |
| WO | 2004076440 A1 | 9/2004 |
| WO | 2005105786 A1 | 11/2005 |
| WO | 2008102145 A2 | 8/2008 |
| WO | 2009047775 A2 | 4/2009 |

OTHER PUBLICATIONS

PCT International Search Report of PCT/IN2007/000466 www.sigmaaldrich.com/catalog/ CAS No. 217087-10-0, 2009.
PCT/IN/2007/000466 Search Report and Notification of Transmittal of the International Search Report and the Written Opinion of the International Searching Authority or the Declaration.

*Primary Examiner* — Patricia Morris
(74) *Attorney, Agent, or Firm* — Ceasar, Rivise, Bernstein, Cohen & Pokotilow, Ltd.

(57) ABSTRACT

The present invention relates to a high assayed esomeprazole magnesium dihydrate substantially free of its trihydrate form. The present invention further provides an improved and commercially viable process for preparation of high assayed esomeprazole magnesium dihydrate substantially free of its trihydrate form. The present invention also provides an improved process for preparation of pure amorphous esomeprazole magnesium. The present invention further provides an improved and commercially viable process for preparation of substantially enantiomerically pure esomeprazole in neutral form or as a pharmaceutically acceptable salt or as its solvates including hydrates. The present invention also provides solid form of esomeprazole calcium salt, its polymorphs (form 1, form 2 and amorphous form) and processes for their preparation thereof.

27 Claims, 4 Drawing Sheets

POLYMORPHS OF ESOMEPRAZOLE SALTS

FIELD OF THE INVENTION

The present invention relates to a high assayed esomeprazole magnesium dihydrate substantially free of its trihydrate form. The present invention further provides an improved and commercially viable process for preparation of high assayed esomeprazole magnesium dihydrate substantially free of its trihydrate form. The present invention also provides an improved process for preparation of pure amorphous esomeprazole magnesium. The present invention further provides an improved and commercially viable process for preparation of substantially enantiomerically pure esomeprazole in neutral form or as a pharmaceutically acceptable salt or as its solvates including hydrates. The present invention also provides solid form of esomeprazole calcium salt, its polymorphs (form 1, form 2 and amorphous form) and processes for their preparation thereof.

BACKGROUND OF THE INVENTION

Omeprazole, chemically 5-methoxy-2-[[(4-methoxy-3,5-dimethyl-2-pyridinyl)methyl]sulfinyl]-1H-benzimidazole and its therapeutic uses are disclosed in European Patent No. 5129. Omeprazole is a well-known gastric acid secretion inhibitor, and is useful as an anti ulcer agent. Omeprazole has a stereogenic center at sulfur and therefore exist as two optical isomers such as R-omeprazole and S-omeprazole (esomeprazole).

PCT Publication No. WO 94/27988 disclosed certain salts (sodium, magnesium, lithium, potassium, calcium and alkyl ammonium salts) of single enantiomers of omeprazole and processes for their preparation thereof. These compounds have improved pharmacokinetic and metabolic properties which will give an improved therapeutic profile such as a lower degree of interindividual variation.

PCT Publication No. WO 96/02535 disclosed a process for the preparation of the single enantiomers of omeprazole and structurally related compounds as well as salts thereof.

PCT Publication No. WO 98/28294 disclosed esomeprazole in an amorphous form, a partly crystalline form A, and a substantially crystalline form B.

U.S. Pat. No. 6,369,085 (herein after referred to as the '085 patent) described crystalline forms of esomeprazole magnesium (esomeprazole magnesium dihydrate Form A, esomeprazole magnesium dihydrate Form B, esomeprazole magnesium trihydrate and esomeprazole potassium) and characterizes them by powder X-ray Diffraction (P-XRD).

According to the '085 patent, esomeprazole magnesium dihydrate Form A is characterized by an X-ray powder diffraction pattern having peaks expressed as d-value at approximately 3.04, 3.14, 3.18, 4.05, 4.19, 4.32, 4.54, 4.69, 5.2, 5.3, 5.8, 6.2, 6.6 and 15.5 A° (Angstrom units); esomeprazole magnesium dihydrate Form B is characterized by an X-ray powder diffraction pattern having peaks expressed as d-value at approximately 4.19, 4.45, 4.68, 4.79, 4.91, 4.98, 5.1, 5.4, 5.5, 5.6, 5.8, 6.3, 6.7, 7.9, 8.1, 11.0, 11.8 and 14.9 A°; esomeprazole magnesium trihydrate is characterized by an X-ray powder diffraction pattern having peaks expressed as d-value at approximately 2.67, 2.79, 3.27, 3.52, 3.82, 3.96, 4.14, 5.2, 5.6, 6.7, 6.9, 8.3 and 16.6 A°; and esomeprazole potassium is characterized by an X-ray powder diffraction pattern having peaks expressed as d-value at approximately 2.31, 2.38, 2.40, 2.43, 2.45, 2.47, 2.52, 2.56, 2.57, 2.58, 2.66, 2.71, 2.76, 2.85, 2.89, 2.93, 2.97, 3.03, 3.06, 3.12, 3.20, 3.28, 3.34, 3.38, 3.42, 3.52, 3.55, 3.60, 3.74, 3.81, 3.87, 3.89, 3.92, 3.98, 4.27, 4.32, 4.42, 4.52, 4.71, 4.75, 5.0, 5.2, 5.3, 5.4, 5.8, 6.1, 6.2, 6.5, 6.8, 7.8, 10.6 and 13.6 A°.

The alkaline salts of omeprazole and (S)-enantiomer of omeprazole (esomeprazole), the pharmaceutical preparations of these salts and the method of treatment of gastric acid-related diseases using them are disclosed in U.S. Pat. Nos. 4,738,974, 5,877,192 and 5,714,504.

PCT Publication No. WO 2004/076440 A1 described crystalline forms, Form I and Form II, of esomeprazole, and its hydrates. PCT Publication No. WO 2004/020436 A1 described amorphous hydrates of esomeprazole magnesium and process for their preparation. PCT Publication No. WO 2004/002982 A2 described amorphous form esomeprazole free base and process for its preparation.

Esomeprazole magnesium dihydrate obtained by the process described in the art, has an important draw back of the being less assayed, and is contaminated with esomeprazole magnesium trihydrate form.

According to the prior art processes, esomeprazole magnesium dihydrate is obtained by using either wet esomeprazole magnesium isolated from aqueous medium, or esomeprazole magnesium trihydrate.

Extensive experimentation is carried out by the present inventors to find the way to eliminate the trihydrate contamination and to prepare high assayed esomeprazole magnesium dihydrate. As a result, it has now been found that high assayed esomeprazole magnesium dihydrate substantially free of its trihydrate impurity can be prepared. The present invention uses neither wet esomeprazole magnesium nor esomeprazole magnesium trihydrate for the preparation of esomeprazole magnesium dihydrate and thereby the present invention could yield esomeprazole magnesium dihydrate substantially free of its trihydrate form.

One object of the present invention is to provide a high assayed esomeprazole magnesium dihydrate substantially free of its trihydrate form.

According to another object of the present invention is to provide an improved and commercially viable process for preparation of high assayed esomeprazole magnesium dihydrate substantially free of its trihydrate form.

Another object of the present invention is to provide an improved process for preparation of pure amorphous esomeprazole magnesium.

According to another object of the present invention is to provide an improved and commercially viable process for preparation of substantially enantiomerically pure esomeprazole in neutral form or as a pharmaceutically acceptable salt or as its solvates including hydrates.

According to another object of the present invention is to provide a solid form of esomeprazole calcium salt.

According to another object of the present invention is to provide stable and novel crystalline forms of esomeprazole calcium salt, processes for preparing them and pharmaceutical compositions comprising them.

According to another object of the present invention is to provide a stable and novel amorphous form of esomeprazole calcium salt, process for preparing it and a pharmaceutical composition comprising it.

DETAILED DESCRIPTION OF THE INVENTION

According to one aspect of the present invention, there is provided a high assayed esomeprazole magnesium dihydrate substantially free of its trihydrate form. The water content of the esomeprazole magnesium dihydrate is between 4.0 and 6.7% by weight, and typically between 4.5 and 5.5% by weight.

According to another aspect of the present invention, there is provided a process for preparation of high assayed esomeprazole magnesium dihydrate substantially free of its trihydrate form, which comprises:

a) (i) adding magnesium chloride or magnesium sulfate to the solution of an alkali metal salt of esomeprazole in an alcoholic solvent; (or)
ii) adding esomeprazole to a solution of magnesium alkoxide in an alcoholic solvent;
b) stirring the mass obtained in step (a);
c) distilling off the alcoholic solvent from the solution;
d) dissolving the residue obtained in step (c) in a chlorinated solvent;
e) filtering the solution formed in step (d);
f) distilling off the chlorinated solvent from the solution obtained in step (e);
g) dissolving the residue obtained in step (f) in a solvent system comprising methanol and water wherein content of water is 2-6 moles per mole of alkali metal salt of esomeprazole used in step (a)(i) or esomeprazole used in step (a)(ii); and
h) precipitating high assayed esomeprazole magnesium dihydrate substantially free of its trihydrate form from the solution obtained in step (g) by adding acetone as an antisolvent.

"High assayed esomeprazole magnesium dihydrate" refers to esomeprazole magnesium dihydrate having the assay of not less than 99%, preferably not less than 99.5% and more preferably between 99.8 and 101%.

The assay of esomeprazole magnesium dihydrate is determined by a suitable High Performance Liquid Chromatograph consisting of a pump an UV-VIS detector, sample injector, controller and integrator or equivalent software. The system is equipped with Inertsil $C_8$ 5 µm 150×4.6 mm column. Assay of esomeprazole magnesium dihydrate is performed by setting HPLC parameters like UV wavelength 300 nm, flow rate of about 1.0 ml/min., and using potassium orthophosphate buffer (mixture of 1.36 gm of potassium dihydrogen orthophosphate and 1.74 gm of di-potassium hydrogen orthophosphate in 1000 ml of water) and acetonitrile as a mobile phase in the ratio of 65:35.

The term "esomeprazole magnesium dihydrate substantially free of trihydrate form" refers to the esomeprazole magnesium dihydrate containing less than about 5% trihydrate form of esomeprazole magnesium by weight, preferably less than about 2% trihydrate form of esomeprazole magnesium by weight, more preferably less than about 1% trihydrate form of esomeprazole magnesium by weight, and still more preferably essentially free of trihydrate form of esomeprazole magnesium. "Essentially free of trihydrate form of esomeprazole magnesium" means that no trihydrate form of esomeprazole magnesium can be detected within the limits of a powder X-ray diffractometer.

The esomeprazole magnesium dihydrate substantially free of its trihydrate form obtained by the process described above is characterized by having X-ray powder diffraction pattern as shown in FIG. 1.

Esomeprazole in neutral form or alkali metal salt of esomeprazole used as starting material may be obtained by processes described in the art, for example by the processes described in the PCT Publication No. WO 94/27988.

Preferable alkali metal salt of esomeprazole used as starting material is sodium or potassium salt of esomeprazole.

The solution of the alkali metal salt of esomeprazole in an alcoholic solvent may be prepared by dissolving alkali metal salt of esomeprazole in an alcoholic solvent at an elevated temperature, preferably at a temperature below 60° C., more preferably at a temperature between 0° C. and 45° C. and still more preferably at a temperature between 5° C. and 40° C.

The term "elevated temperature" refers to the temperature at which the esomeprazole or alkali metal salt of esomeprazole can be freely dissolvable in the alcoholic solvent.

Preferable alcoholic solvent used in step (a)(i) or step (a)(ii) is methanol or ethanol, and more preferable alcoholic solvent is methanol.

The magnesium chloride or magnesium sulfate in step (a)(i) is added to the solution of an alkali metal salt of esomeprazole at a temperature below 60° C., more preferably added at a temperature between 0° C. and 45° C. and still more preferably added at a temperature between 15° C. and 40° C.

Preferably anhydrous form of magnesium chloride or magnesium sulfate is used in step (a)(i) and more preferably the solution of anhydrous form of magnesium chloride or magnesium sulfate in methanol is used.

The esomeprazole in step (a)(ii) is added to the solution of magnesium alkoxide in an alcoholic solvent at a temperature below 60° C., more preferably added at a temperature between 0° C. and 45° C. and still more preferably added at a temperature between 15° C. and 40° C.

Preferable magnesium alkoxide used in step (a)(ii) is magnesium methoxide or magnesium ethoxide, and more preferable magnesium alkoxide is magnesium methoxide.

The reaction mass in step (b) is preferably stirred at least for about 15 minutes, more preferably stirred at least for about 20 minutes and still more preferably stirred for about 20 minutes to 1 hour.

The reaction mass in step (b) is preferably stirred at a temperature below 50° C., more preferably stirred at a temperature between 0° C. and 45° C. and still more preferably stirred at a temperature between 15° C. and 40° C.

The distillation of the alcoholic solvent in step (c) is preferably carried out under vacuum at a temperature below 55° C., more preferably carried out under vacuum at a temperature below 50° C. and still more preferably carried out under vacuum at a temperature between 30° C.-45° C.

The residue in step (d) is preferably dissolved in the chlorinated solvent at a temperature below 60° C., more preferably dissolved at a temperature between 0° C. and 45° C. and still more preferably dissolved at a temperature between 15° C. and 40° C.

Preferable chlorinated solvent used in step (d) is methylene dichloride or chloroform and more preferable chlorinated solvent is methylene dichloride.

The distillation of the chlorinated solvent in step (f) is preferably carried out under vacuum at a temperature below 55° C., more preferably carried out under vacuum at a temperature below 50° C. and still more preferably carried out under vacuum at a temperature between 30° C.-45° C.

The residue in step (g) is preferably dissolved in the solvent system comprising methanol and water at a temperature below 60° C., more preferably dissolved at a temperature between 0° C. and 45° C. and still more preferably dissolved at a temperature between 15° C. and 40° C.

Preferably the content of water in the solvent system comprising methanol and water in step (g) is 2.5-5.5 moles per mole of alkali metal salt of esomeprazole used in step (a)(i) or esomeprazole used in step (a)(ii), and more preferably the content of water is 3-5 moles per mole of alkali metal salt of esomeprazole used in step (a)(i) or esomeprazole used in step (a)(ii).

The precipitated high assayed esomeprazole magnesium dihydrate substantially free of its trihydrate form in step (h) is collected by conventional methods such as filtration or centrifugation.

According to another embodiment of the present invention, there is provided a process for preparation of amorphous esomeprazole magnesium, which comprises:
a) reacting an alkali metal salt of esomeprazole with magnesium chloride in aqueous medium; and
b) filtering or centrifuging the reaction mass to obtain amorphous form of esomeprazole magnesium, the said process is characterized in that the reaction mass is not stirred before filtering or centrifuging the reaction mass.

Preferable alkali metal salt of esomeprazole used as starting material is sodium or potassium salt of esomeprazole.

According to another embodiment of the present invention, there is provided substantially enantiomerically pure esomeprazole calcium salt.

The term "substantially enantiomerically pure esomeprazole calcium salt" refers to esomeprazole calcium salt having the content of isomeric impurity (R-omeprazole) in less than about 0.5% by weight measured by High Performance Liquid Chromatography (HPLC), preferably less than about 0.1% by weight, more preferably less than about 0.05% by weight and still more preferably having no traces of the isomeric impurity.

According to another embodiment of the present invention, there is provided a process for preparing substantially enantiomerically pure esomeprazole or a pharmaceutically acceptable salt thereof from enantiomerically impure esomeprazole calcium salt; which comprises:
a) dissolving enantiomerically impure esomeprazole calcium salt in an alcoholic solvent;
b) isolating substantially enantiomerically pure esomeprazole calcium salt as a crystalline solid; and
c) neutralizing the enantiomerically pure esomeprazole calcium salt formed in step (b) with an acid to obtain substantially enantiomerically pure esomeprazole and optionally converting esomeprazole formed into pharmaceutically acceptable slats of esomeprazole.

The term "substantially enantiomerically pure esomeprazole or a pharmaceutically acceptable salt thereof" refers to the esomeprazole or a pharmaceutically acceptable thereof having the content of isomeric impurity (R-omeprazole) in less than about 0.1% by weight measured by HPLC, preferably less than about 0.05% by weight and still more preferably having no traces of the isomeric impurity.

The term "enantiomerically impure esomeprazole calcium salt" refers to the esomeprazole calcium salt having the content of isomeric impurity (R-omeprazole) in about above 0.5% and up to 30% by weight.

Preferable alcoholic solvent used in step (a) is methanol or ethanol, and more preferable alcoholic solvent is methanol.

The enantiomerically impure esomeprazole calcium salt in step (a) is preferably dissolved in the alcoholic solvent at a temperature below 60° C., more preferably dissolved at a temperature between 0° C. and 55° C. and still more preferably dissolved at a temperature between 30° C. and 50° C.

Isolation of enantiomerically pure esomeprazole calcium salt in step (b) may be carried out by methods usually known in the art such as cooling, partial removal of the solvent from the solution, addition of an anti-solvent or a combination thereof. More preferably the isolation in step (b) is carried out by cooling or by adding an anti-solvent. Preferable anti-solvents are diisopropyl ether, dibutyl ether, tert-butylmethyl ether, n-heptane, n-hexane, cyclohexane, toluene, xylene, ethyl acetate and water.

The acid used in step (c) may be an organic or inorganic acid. Preferable organic acid is selected from the group consisting of carboxylic acids such as acetic acid and formic acid; and sulfonic acids such as methane sulfonic acid.

Most preferable organic acid is acetic acid. Preferable inorganic acid is a mineral acid such as sulfuric acid, hydrochloric acid and phosphoric acid.

Preferably aqueous solution of acid may be used for neutralization and more preferably dilute aqueous acid may be used.

The neutralization reaction in step (c) may preferably be carried out in a solvent system containing water and an organic solvent. Suitable organic solvent is selected from the group consisting of ester solvents such as ethyl acetate, methyl acetate, isopropyl acetate, tert-butyl methyl acetate and ethyl formate; halogenated hydrocarbon solvents such as methylene dichloride, chloroform, carbontetrachloride, ethylene dichloride; and hydrocarbon solvents such as benzene, toluene, xylene. More preferable organic solvent is methylene dichloride, chloroform or ethyl acetate.

The neutralization reaction in step (c) may preferably be carried out at a temperature below 40° C., more preferably carried out between 0° C. and 30° C. and still more preferably carried out between 0° C. and 20° C.

The enantiomerically pure esomeprazole obtained in step (c) can be converted into pharmaceutically acceptable salts by conventional methods.

Preferable pharmaceutically acceptable salts of esomeprazole are those of lithium, sodium, potassium, magnesium, and their solvates including hydrates thereof.

Enantiomerically impure esomeprazole calcium salt used as starting material may be obtained by process described in the art, for example by the process described in the PCT Publication No. WO 94/27988.

According to another embodiment of the present invention, there is provided a solid form of esomeprazole calcium salt.

According to another embodiment of the present invention, there is provided a novel crystalline form of esomeprazole calcium salt, designated as esomeprazole calcium salt form 1, characterized by an X-ray powder diffraction pattern having peaks expressed as 2-theta angle positions at about 5.4, 11.4, 12.2, 13.1, 13.3, 14.7, 16.8, 20.3, 21.6, 22.4, 24.5 and 25.5±0.2 degrees. The typical X-ray powder diffraction spectrum of esomeprazole calcium form 1 is shown in FIG. 2.

According to another embodiment of the present invention, there is provided a process for preparation of esomeprazole calcium salt form 1, which comprises:
a) reacting an alkali metal salt of esomeprazole with calcium chloride in aqueous medium; and
b) isolating esomeprazole calcium salt form 1 from the reaction mass obtained in step (a).

Preferable alkali metal salt of esomeprazole used in step (a) is sodium or potassium salt of esomeprazole.

The reaction mass in step (a) is preferably stirred at least for about 15 minutes, more preferably stirred at least for about 30 minutes and still more preferably stirred for about 30 minutes to 3 hours.

The reaction mass in step (a) is preferably stirred at a temperature below 50° C., more preferably stirred at a temperature between 0° C. and 45° C. and still more preferably stirred at a temperature between 15° C. and 40° C.

Isolation of esomeprazole calcium salt form 1 in step (b) may be carried out by methods usually known in the art such as cooling, partial removal of the solvent from the solution, addition of an anti-solvent or a combination thereof.

The esomeprazole calcium salt form 1 obtained by the process described above is having water content of between 11 and 13.5% by weight, and typically between 11.5 and 12.5% by weight.

According to another embodiment of the present invention, there is provided a novel crystalline form of esomeprazole calcium salt, designated as esomeprazole calcium salt form 2, characterized by an X-ray powder diffraction pattern having peaks expressed as 2-theta angle positions at about 5.3, 6.1, 12.4, 12.5, 13.7, 15.3, 15.6, 16.3, 16.7, 17.6, 19.6, 21.9, 22.7, 23.6, 24.2, 25.1, 25.4, 27.1, 29.5, 30.5, 31.5, 31.8, 33.0, 33.5, 35.5, 35.7 and 36.0±0.2 degrees. The typical X-ray powder diffraction spectrum of esomeprazole calcium salt form 2 is shown in FIG. 3.

According to another embodiment of the present invention, there is provided a process for the preparation of esomeprazole calcium salt form 2, which comprises:
a) dissolving esomeprazole calcium salt form 1 in an alcoholic solvent; and
b) isolating esomeprazole calcium salt form 2 from the solution obtained in step (a).

Preferable alcoholic solvent used in step (a) is methanol or ethanol, and more preferable alcoholic solvent is methanol.

The esomeprazole calcium salt form 1 in step (a) is preferably dissolved in the alcoholic solvent at a temperature below 60° C., more preferably dissolved at a temperature between 0° C. and 55° C. and still more preferably dissolved at a temperature between 30° C. and 50° C.

Isolation of esomeprazole calcium salt form 2 in step (b) may be carried out by methods usually known in the art such as cooling, partial removal of the solvent from the solution, addition of an anti-solvent or a combination thereof. More preferably the isolation in step (b) is carried out by cooling or by adding an anti-solvent. Preferable anti-solvents are diisopropyl ether, dibutyl ether, tert-butylmethyl ether, n-heptane, n-hexane, cyclohexane, toluene, xylene, ethyl acetate and water.

The esomeprazole calcium salt form 2 obtained by the process described above is having water content of between 8 and 11% by weight, and typically between 9 and 10% by weight.

According to another embodiment of the present invention, there is provided an amorphous form of esomeprazole calcium salt, designated as amorphous esomeprazole calcium, characterized by having broad X-ray diffraction spectrum as shown in FIG. 4.

According to another embodiment of the present invention, a process is provided for the preparation of amorphous esomeprazole calcium, which comprises drying any crystalline form of esomeprazole calcium salt at least for about 20 hours at a temperature of about 40-55° C.

Preferably the crystalline form of esomeprazole calcium is dried for about 22 hours and up to 30 hours at 45-50° C. under vacuum.

The amorphous esomeprazole calcium obtained by the process described above is having water content of between 6 and 8% by weight, and typically between 6.5 and 7.5% by weight.

According to another embodiment of the present invention, there is provided another process for the preparation of amorphous esomeprazole calcium, which comprises:
a) dissolving crystalline esomeprazole calcium salt in a solvent selected from acetone, isopropyl acetate and a mixture thereof; and
b) isolating amorphous esomeprazole calcium salt from the solution obtained in step (a).

The crystalline esomeprazole calcium salt used in step (a) is crystalline form 1 or form 2 of esomeprazole calcium salt.

The crystalline esomeprazole calcium salt in step (a) is preferably dissolved in the solvent at a temperature below 60° C., more preferably dissolved at a temperature between 0° and 55° C. and still more preferably dissolved at a temperature between 30° C. and 50° C.

Isolation of amorphous esomeprazole calcium salt in step (b) may be carried out by methods usually known in the art such as cooling, partial removal of the solvent from the solution, addition of an anti-solvent or a combination thereof. More preferably the isolation in step (b) is carried out by cooling or by adding an anti-solvent. Preferable anti-solvent is selected from the group consisting of n-heptane, n-hexane and cyclohexane.

According to another aspect of the present invention there is provided a pharmaceutical composition comprising esomeprazole calcium crystalline form 1 and a pharmaceutically acceptable excipient.

Preferable pharmaceutical composition of esomeprazole calcium crystalline form 1 is selected from a solid oral dosage form and oral suspension.

According to another aspect of the present invention there is provided a pharmaceutical composition comprising esomeprazole calcium crystalline form 2 and a pharmaceutically acceptable excipient.

Preferable pharmaceutical composition of esomeprazole calcium crystalline form 2 is selected from a solid oral dosage form and oral suspension.

According to another aspect of the present invention there is provided a pharmaceutical composition comprising amorphous esomeprazole calcium and a pharmaceutically acceptable excipient.

Preferable pharmaceutical composition of amorphous esomeprazole calcium is selected from a solid oral dosage form and oral suspension.

Figure 1:
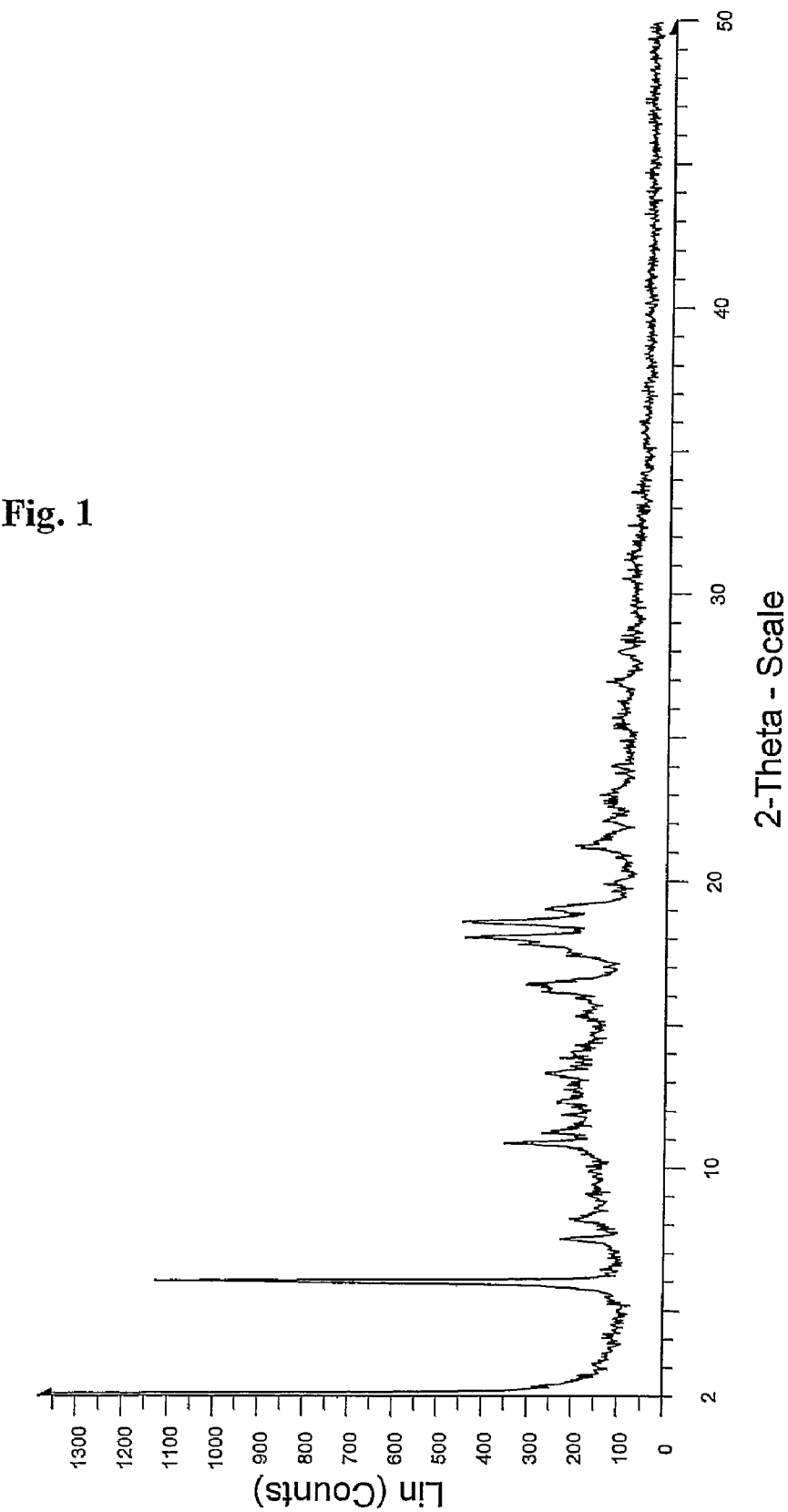
FIG. 1 shows a typical X-ray powder diffraction spectrum of esomeprazole magnesium dihydrate substantially free of its trihydrate form obtained as per the process described in example 1 of the present invention.
Figure 2:
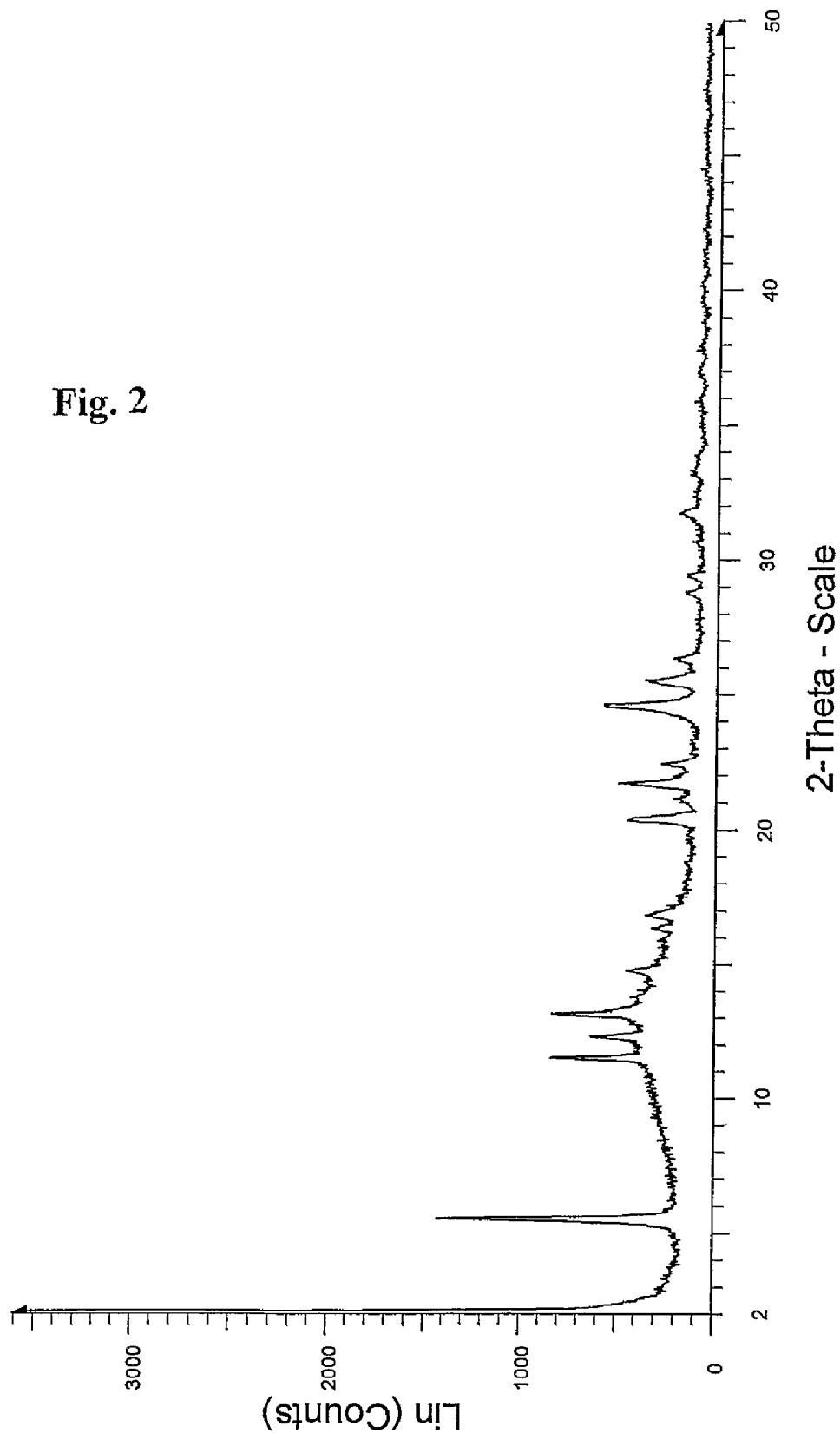
FIG. 2 shows a typical X-ray powder diffraction spectrum of esomeprazole calcium salt crystalline form 1.
Figure 3:
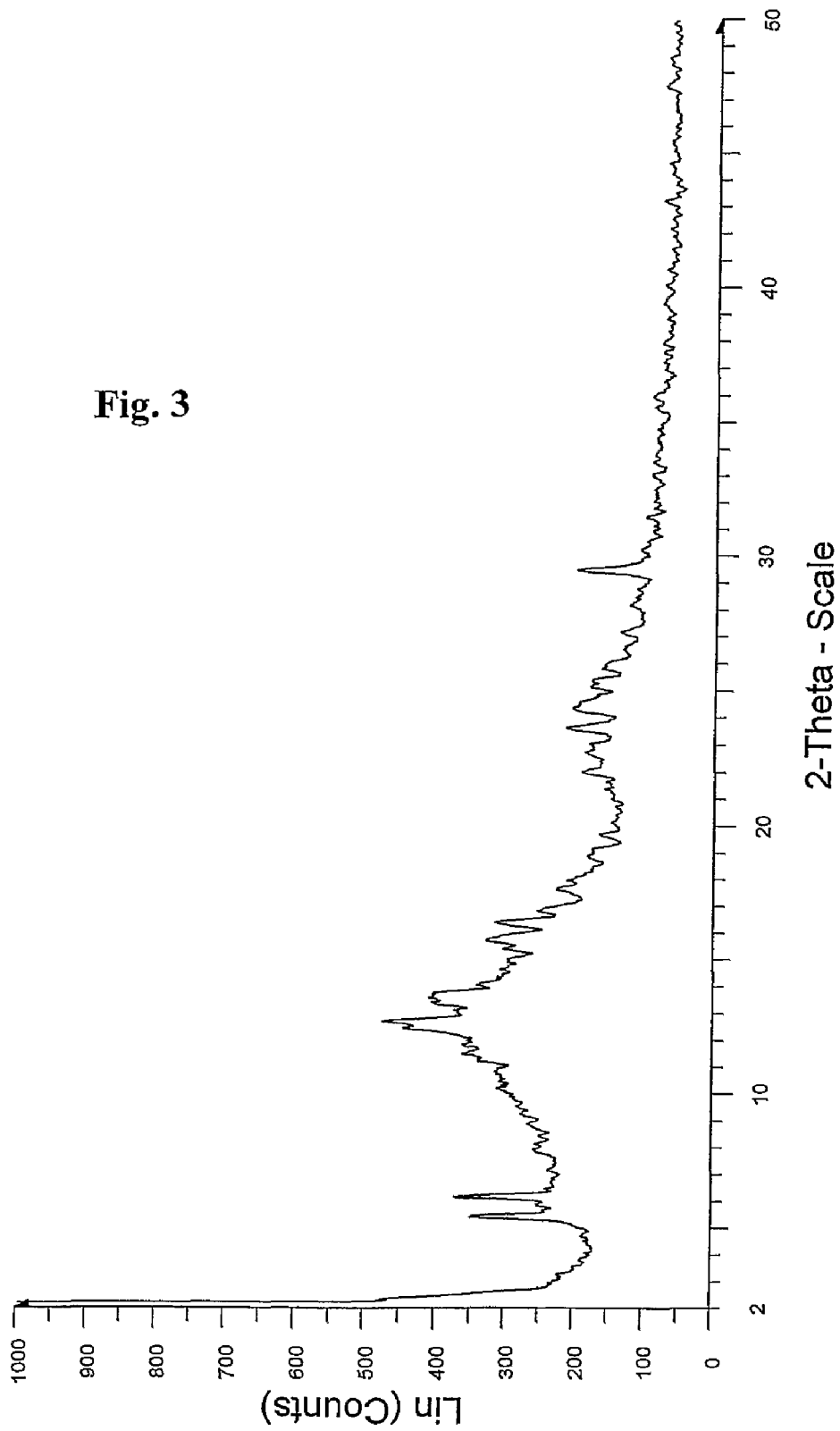
FIG. 3 shows a typical X-ray powder diffraction spectrum of esomeprazole calcium salt crystalline form 2.
Figure 4:
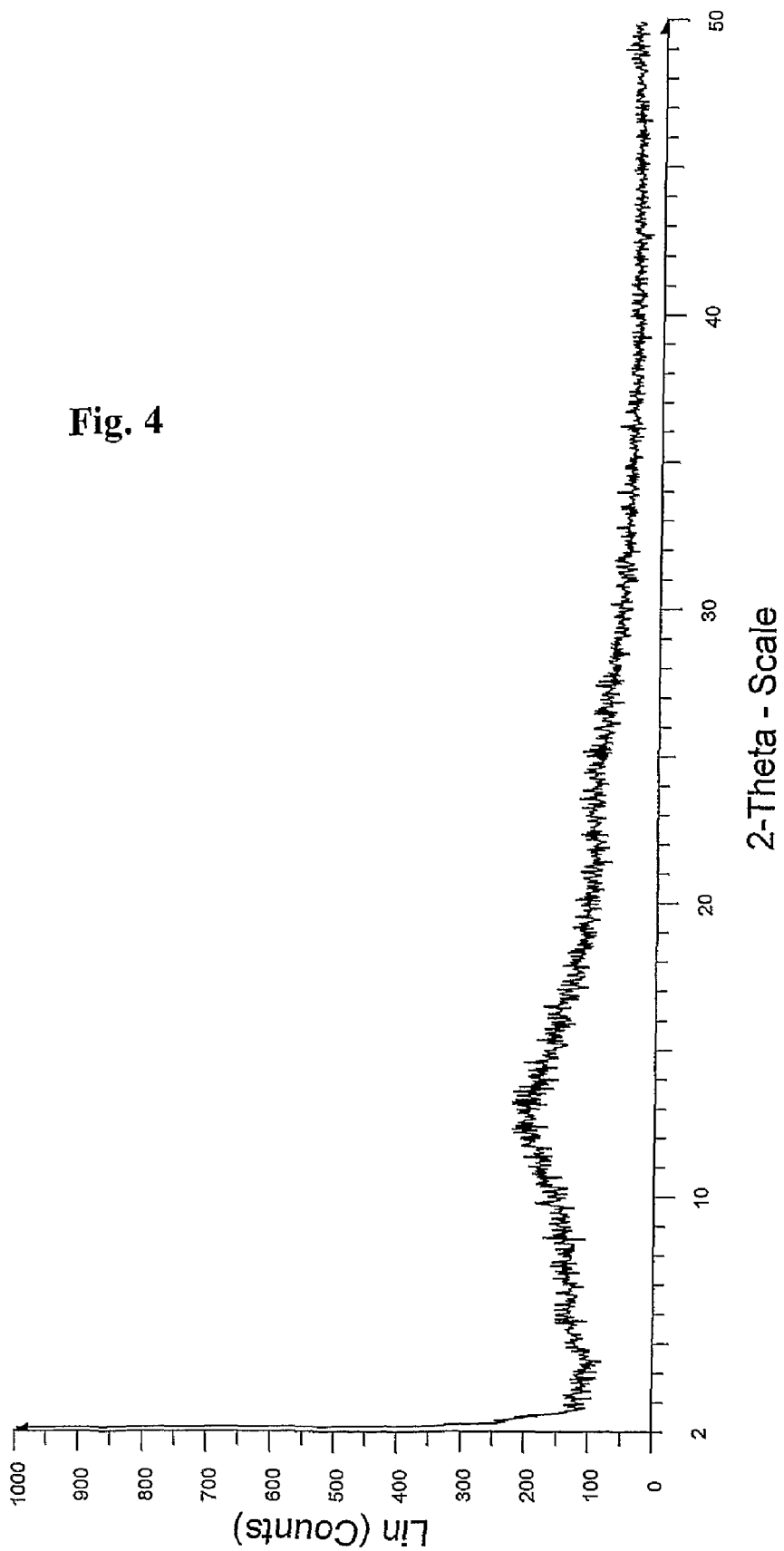
FIG. 4 shows a typical X-ray powder diffraction spectrum of amorphous esomeprazole calcium salt.

X-ray powder diffraction spectrum was measured on a bruker axs D8 advance X-ray powder diffractometer having a copper-$k_\alpha$ radiation. Approximately 1 gm of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and 35 mA.

The following examples are given for the purpose of illustrating the present invention and should not be considered as limitations on the scope or spirit of the invention.

REFERENCE EXAMPLES

Reference Example 1

Esomeprazole (100 gm) is dissolved in methanol (150 ml) at 25-30° C., the solution is cooled to 10° C. and then the solution of sodium hydroxide (13 gm) in methanol (135 ml) is added for 15 minutes at 10-15° C. The mass temperature is raised to 25-30° C., stirred for 10 hours at 25-30° C., the resulting mass is cooled to 10° C. and then stirred for 1 hour at 10-15° C. Filtered the solid, washed the bed with chilled methanol and then dried at 45-50° C. to give 66 gm of esomeprazole sodium salt.

Reference Example 2

Esomeprazole sodium (21 gm, obtained as per the process described in reference example 1) is dissolved in water (273 ml) at 25-30° C. and then the solution of $MgCl_2.6H_2O$ (5.9 gm) in water (32 ml) is slowly added for 40 minutes at 25-30° C. (reaction mass pH is 9.5-9.8). The reaction mass is stirred for 1 hour at 25-30° C., filtered the bed and washed with water (30 ml). The solid obtained (the P-XRD pattern of this solid is matched with trihydrate form of esomeprazole magnesium) is dissolved in methanol (170 ml) at 25-30° C., stirred for 10 minutes and then subjected to carbon treatment at 25-30° C. The resulting filtrate is distilled under vacuum at below 50° C. and then co-distilled with acetone (180 ml). To the residue added acetone (68 ml), stirred for 20 minutes at 40° C., cooled the mass to 25° C. and then stirred for 30 minutes. The resulting mass is further cooled to 10° C. and stirred for 30 minutes at 5-10° C. Filtered the material, washed with acetone (10 ml) and then dried at 45-50° C. to give 13.5 gm of esomeprazole magnesium dihydrate (Assay by HPLC: 98.5%; content of trihydrate form: 8%).

EXAMPLES

Example 1

Esomeprazole sodium (15 gm, obtained as per the process described in reference example 1) is dissolved in methanol (150 ml), stirred for 10 minutes at 25-30° C., to the solution added a solution of anhydrous $MgCl_2$ (2 gm) in methanol (150 ml) for 5-10 minutes at 25-30° C. and then stirred for 30 minutes at 25-30° C. Distilled off methanol completely under vacuum at below 40° C. and then co-distilled two times with methylene dichloride (each time 150 ml). To the residue added methylene dichloride (750 ml) and anhydrous $Na_2SO_4$ (30 gm) at 25-30° C., the contents are stirred for 15 minutes, the resulting mass is passed on hi-flow and washed the bed with methylene dichloride (150 ml). The resulting filtrate is distilled under vacuum at below 40° C. and then co-distilled with methanol (75 ml). To the resulting residue added methanol (135 ml) and water (3 ml), stirred for 15 minutes at 25-30° C. and then distilled under vacuum at below 40° C. until the mass volume reaches to 30 ml. To the resulting mass added acetone (60 ml) slowly at 35-40° C., stirred for 10 minutes, and again added acetone (60 ml), stirred for 10 minutes and then cooled to 25° C. The mass is stirred for 2 hours at 20-25° C., further cooled down to 5° C. and stirred for 30 minutes at 5-10° C. Filtered the material, washed with acetone (15 ml) and then dried at 45-50° C. for 4-5 hours to give 7.9 gm of esomeprazole magnesium dihydrate (Assay by HPLC:100%; content of trihydrate form: Not detected).

Example 2

Magnesium turnings (1.02 gm) are dissolved and reacted with methanol (90 ml) at 40° C. with a catalytic amount of methylene dichloride, the resulting solution is stirred for 5-6 hours at 35-40° C. under nitrogen atmosphere and then cooled to 25-30° C. To the resulting magnesium methoxide solution added esomeprazole (30 gm) and then the contents are stirred for 30 minutes at 25-30° C. Distilled off methanol completely under vacuum at below 40° C. and then co-distilled two times with methylene dichloride (each time 150 ml). To the residue added methylene dichloride (1500 ml) and anhydrous $Na_2SO_4$ (30 gm) at 25-30° C., the contents are stirred for 15 minutes, the resulting mass is passed on hi-flow and washed the bed with methylene dichloride (150 ml). The resulting filtrate is distilled under vacuum at below 40° C. and then co-distilled with methanol (75 ml). To the resulting residue added methanol (240 ml) and water (4.5 ml), stirred for 15 minutes at 25-30° C. and then distilled under vacuum at below 40° C. until the mass volume reaches to 60 ml. To the resulting mass added acetone (100 ml) slowly at 35-40° C., stirred for 10 minutes, and again added acetone (120 ml), stirred for 10 minutes and then cooled to 25° C. The mass is stirred for 2 hours at 20-25° C., further cooled down to 5° C. and stirred for 30 minutes at 5-10° C. Filtered the material, washed with acetone (30 ml) and then dried at 45-50° C. for 4-5 hours to give 16.8 gm of esomeprazole magnesium dihydrate (Assay by HPLC: 99.7%; content of trihydrate form: Not detected).

Example 3

Esomeprazole sodium (6 gm) is dissolved in water (108 ml) at 20-25° C. and then added a solution of $MgCl_2.6H_2O$ (1.68 gm) in water (72 ml) drop wise at 20-25° C. Centrifuged the material at 25° C. and then dried the material at 45-50° C. to give 4.5 gm of amorphous esomeprazole magnesium.

Example 4

Step-I
Esomeprazole sodium (20 gm, enantiomeric purity: 82%) is dissolved in water (200 ml) and then stirred for 10 minutes at 25-30° C. To the solution added a solution of calcium chloride (6 gm) in water (100 ml) for 15 minutes and stirred for 2 hours at 25-30° C. Filtered the solid, washed with water (40 ml) and then dried at 45-50° C. for 5-6 hours to give 18.2 gm of enantiomerically impure esomeprazole calcium salt (enantiomeric purity: 82%).

Step-II
Enantiomerically impure esomeprazole calcium salt (18.2 gm, obtained in step-I) is dissolved in methanol (108 ml) at 25-30° C., the solution is heated to 45° C. and stirred for 30 minutes at 40-45° C. The solution is cooled to 20° C. and stirred for 1 hour at 20-25° C. The resulting solution is further cooled to 0° C. and then stirred for 1 hour at 0-5° C. Filtered the solid, washed with chilled methanol (18 ml) and then dried at 45-50° C. for 4-5 hours to give 13 gm of enantiomerically pure esomeprazole calcium salt (enantiomeric purity: 99.7%).

Step-III
Methylene dichloride (130 ml) and water (65 ml) are added to enantiomerically pure esomeprazole calcium salt (13 gm, obtained in step-II) under stirring at 25-30° C., the contents are cooled to 15° C. and then pH of the mass is adjusted to 7.0-7.5 with acetic acid. The resulting mass is stirred for 15 minutes, separated the layers and the aqueous layer is extracted with methylene dichloride (100 ml). The total organic layer is washed with 5% NaCl solution (65 ml), dried over sodium sulfate and the resulting organic layer is distilled under vacuum at 40° C. and then co-distilled with methanol (100 ml) to give 10.3 gm of enantiomerically pure esomeprazole as residue (enantiomeric purity: 100%).

Step-IV

The enantiomerically pure esomeprazole obtained in step-III can be converted to esomeprazole magnesium dihydrate as per the process described in example-2.

Example 5

Esomeprazole sodium (20 gm) is dissolved in water (200 ml) and then stirred for 10 minutes at 25-30° C. To the solution added a solution of calcium chloride (6 gm) in water (100 ml) for 15 minutes and stirred for 2 hours at 25-30° C. Filtered the solid, washed with water (40 ml) and then dried at 45-50° C. for 5-6 hours to give 18.2 gm of esomeprazole calcium salt crystalline form 1.

Example 6

Esomeprazole calcium crystalline form 1 (18.2 gm, obtained by the process described in example 5) is dissolved in methanol (108 ml) at 25-30° C., the solution is heated to 45° C. and stirred for 30 minutes at 40-45° C. The solution is cooled to 20° C. and stirred for 1 hour at 20-25° C. The resulting solution is further cooled to 0° C. and then stirred for 1 hour at 0-5° C. Filtered the solid, washed with chilled methanol (18 ml) and then dried at 45-50° C. for 4-5 hours to give 13 gm of esomeprazole calcium salt crystalline form 2.

Example 7

Esomeprazole calcium salt crystalline form 2 (10 gm) is dried at 45-50° C. under vacuum for 24-25 hours to give amorphous esomeprazole calcium quantitatively.

Example 8

Esomeprazole calcium crystalline form 1 (3 gm) is dissolved in isopropyl acetate (450 ml) at 45-50° C. to form a clear solution, stirred for 1 hour and then cooled to 30-35° C. Distilled 300 ml of isopropyl acetate under vacuum at below 35° C., the remaining mass is cooled to 20° C. and then stirred for 30 minutes at 20-25° C. Cooled the mass to 10° C. and stirred for 1 hour at 10-15° C. Filtered the solid, washed with isopropyl acetate (9 ml) and then dried at 45-50° C. to give 2.5 gm of amorphous esomeprazole calcium salt.

Example 9

Esomeprazole calcium crystalline form 2 (3 gm) is dissolved acetone (100 ml) at 25° C., stirred for 15 minutes at 25-30° C. The resulting mass is passed on hi-flo, washed the bed with acetone (10 ml), to the filtrate slowly added n-hexane (220 ml) for 30 minutes at 25-30° C. and then stirred for 30 minutes at the same temperature. Filtered the material, washed with the mixture of acetone (5 ml) and n-hexane (5 ml) and then dried at 45-50° C. to give 2.2 gm of amorphous esomeprazole calcium salt.

We claim:

1. A process for preparation of high assayed esomeprazole magnesium dihydrate substantially free of its trihydrate form, which comprises:
   a) (i) adding magnesium chloride or magnesium sulfate to the solution of an alkali metal salt of esomeprazole in an alcoholic solvent; (or)
      (ii) adding esomeprazole to a solution of magnesium alkoxide in an alcoholic solvent;
   b) stirring the mass obtained in step (a);
   c) distilling off the alcoholic solvent from the solution;
   d) dissolving the residue obtained in step (c) in a chlorinated solvent;
   e) filtering the solution formed in step (d);
   f) distilling off the chlorinated solvent from the solution obtained in step (e);
   g) dissolving the residue obtained in step (f) in a solvent system comprising methanol and water wherein the content of water is 2-6 moles per mole of alkali metal salt of esomeprazole used in step (a)(i) or esomeprazole used in step (a)(ii); and
   h) precipitating high assayed esomeprazole magnesium dihydrate substantially free of its trihydrate form from the solution obtained in step (g) by adding acetone as an anti-solvent.

2. The process as claimed in claim 1, wherein the alkali metal salt of esomeprazole used in step (a)(i) is a sodium or potassium salt of esomeprazole.

3. The process as claimed in claim 1, wherein the alcoholic solvent used in step (a)(i) or step (a)(ii) is methanol or ethanol.

4. The process as claimed in claim 3, wherein the alcoholic solvent is methanol.

5. The process as claimed in claim 1, wherein an anhydrous form of magnesium chloride or magnesium sulfate is used in step (a)(i).

6. The process as claimed in claim 5, wherein a solution of an anhydrous form of magnesium chloride or magnesium sulfate in methanol is used.

7. The process as claimed in claim 1, wherein the magnesium alkoxide used in step (a)(ii) is magnesium methoxide or magnesium ethoxide.

8. The process as claimed in claim 7, wherein the magnesium alkoxide is magnesium methoxide.

9. The process as claimed in claim 1, wherein the reaction mass in step (b) is stirred at least for about 15 minutes.

10. The process as claimed in claim 9, wherein the reaction mass is stirred for about 20 minutes to 1 hour.

11. The process as claimed in claim 1, wherein the reaction mass in step (b) is stirred at a temperature below 50° C.

12. The process as claimed in claim 11, wherein the reaction mass is stirred at a temperature between 0° C. and 45° C.

13. The process as claimed in claim 12, wherein the reaction mass is stirred at a temperature between 15° C. and 40° C.

14. The process as claimed in claim 1, wherein the residue in step (d) is dissolved in the chlorinated solvent at a temperature below 60° C.

15. The process as claimed in claim 14, wherein the residue is dissolved at a temperature between 0° C. and 45° C.

16. The process as claimed in claim 15, wherein the residue is dissolved at a temperature between 15° C. and 40° C.

17. The process as claimed in claim 1, wherein the chlorinated solvent used in step (d) is methylene dichloride or chloroform.

18. The process as claimed in claim 17, wherein the chlorinated solvent is methylene dichloride.

19. The process as claimed in claim 1, wherein the distillation of the chlorinated solvent in step (f) is carried out under vacuum at a temperature below 55° C.

20. The process as claimed in claim 19, wherein the distillation is carried out under vacuum at a temperature below 50° C.

21. The process as claimed in claim 20, wherein the distillation is carried out under vacuum at a temperature between 30° C.-45° C.

22. The process as claimed in claim 1, wherein the residue in step (g) is dissolved in the solvent system comprising methanol and water at a temperature below 60° C.

23. The process as claimed in claim 22, wherein the residue is dissolved at a temperature between 0° C. and 45° C.

24. The process as claimed in claim 23, wherein the residue is dissolved at a temperature between 15° C. and 40° C.

25. The process as claimed in claim 1, wherein the content of water in the solvent system comprising methanol and water in step (g) is 2.5-5.5 moles per mole of alkali metal salt of esomeprazole used in step (a)(i) or esomeprazole used in step (a)(ii).

26. The process as claimed in claim 25, wherein the content of water is 3-5 moles per mole of alkali metal salt of esomeprazole used in step (a)(i) or esomeprazole used in step (a)(ii).

27. The process as claimed in claim 1, wherein the precipitated high assayed esomeprazole magnesium dihydrate substantially free of its trihydrate form in step (h) is collected by filtration or centrifugation.

* * * * *